(12) United States Patent
Halavee (10) Patent No.: US 6,324,257 B1
(45) Date of Patent: Nov. 27, 2001

(54) RADIOTHERAPEUTICAL DEVICE AND USE THEREOF

(75) Inventor: Uriel Halavee, Ramat-Gan (IL)

(73) Assignee: X-Technologies Inc. (IL)

( * ) Notice: Subject to any disclaimer, the term of this patent is extended or adjusted under 35 U.S.C. 154(b) by 0 days.

(21) Appl. No.: 09/325,703

(22) Filed: Jun. 3, 1999

Related U.S. Application Data
(60) Provisional application No. 60/087,970, filed on Jun. 4, 1998.

(51) Int. Cl.[7] .................................................. H01J 35/06
(52) U.S. Cl. ......................... 378/121; 378/136; 378/143
(58) Field of Search ............................. 378/65, 64, 136, 378/119, 121, 145, 204, 143; 604/20, 21; 600/1

(56) References Cited

U.S. PATENT DOCUMENTS

| Re. 34,421 | 10/1993 | Parker . | |
|---|---|---|---|
| 3,777,124 | 12/1973 | Pavkovich . | |
| 4,976,266 | 12/1990 | Huffman et al. . | |
| 5,090,043 | 2/1992 | Parker et al. | 378/121 |
| 5,153,900 | 10/1992 | Nomikos et al. | 378/65 |
| 5,243,638 | 9/1993 | Wang et al. | 378/119 |
| 5,422,926 | 6/1995 | Smith et al. | 378/121 |
| 5,428,658 | 6/1995 | Oettinger . | |
| 5,528,652 | 6/1996 | Smith et al. | 378/65 |
| 5,547,454 | 8/1996 | Horn et al. . | |
| 5,566,221 | 10/1996 | Smith et al. | 378/145 |
| 5,621,780 | 4/1997 | Smith et al. | 378/65 |
| 5,729,583 | 3/1998 | Tang . | |
| 5,854,922 | 12/1998 | Chornenky . | |
| 5,910,102 | 6/1999 | Hastings . | |
| 5,984,853 | 11/1999 | Smith | 600/1 |

FOREIGN PATENT DOCUMENTS

| 0 860 180 A2 | 8/1998 | (EP) . |
| 0 860 181 A2 | 8/1998 | (EP) . |
| 0 860 180 A3 | 4/1999 | (EP) . |
| 0 860 181 A3 | 4/1999 | (EP) . |
| WO 97/07740 | 3/1997 | (WO) . |
| WO 98/36796 | 8/1998 | (WO) . |
| WO 99/09580 | 2/1999 | (WO) . |
| WO 99/36938 | 7/1999 | (WO) . |
| WO 99/44687 | 9/1999 | (WO) . |
| WO 99/45562 | 9/1999 | (WO) . |
| WO 99/45563 | 9/1999 | (WO) . |

*Primary Examiner*—David P. Porta
(74) *Attorney, Agent, or Firm*—Rossi & Associates (57) ABSTRACT

The present invention related to miniaturized x-ray tubes, that enable radiation treatment by locating the x-ray source within a human body in close vicinity to or inside of the area to be treated with X-rays. Advantageously, the present invention eliminates most of the problems related to the methods based on a radioactive source and offers a method for efficient and controllable radiation treatment.

5 Claims, 10 Drawing Sheets

RADIOTHERAPEUTICAL DEVICE AND USE THEREOF

This application claims benefit of No. 60/087,970 filed Jun. 4, 1998.

FIELD OF THE INVENTION

The present invention relates to a device and method for radiotherapy, specifically for minimally invasive radiation treatment such as tumor radiation treatment and intravascular x-ray irradiation treatment for the prevention of restenosis in blood vessels.

BACKGROUND OF THE INVENTION

The fast growing field of brachytherapy utilizes radiation sources, such as beta emitters, gamma emitters and x-ray sources, for introduction into body cavities or organs, for radiotherapy. The object of radiotherapy is to produce biological damage of a controlled volume of tissue e.g., a tumor, while avoiding damaging adjacent normal tissues. In this method relatively high doses of x-rays, high energy charged particle beams or gamma rays emitted by radioactive isotopes irradiate diseased and normal tissues. The irradiated cells are damaged and die or are unable to reproduce.

Brachytherapy procedures include implanting radioactive sources in various shapes into specific organs or locations in the human body for prolonged irradiation treatment or introducing the radiation source via a suitable catheter or probe in cases where lower doses or short irradiation periods are required. Brachytherapy is applied in tumor therapy and usually involves the introduction of radioactive sources for radiation treatment into tumors or their vicinity in body cavities.

Another major evolving application in brachytherapy is the procedure of endovascular brachytherapy. Endovascular brachytherapy is intravascular irradiation treatment for prevention of restenosis, which occurs after angioplasty in coronary blood vessels by means of balloons and stents. The estimated number of angioplasty procedures in the U.S. is 500000 P/A with restenosis occurring in about 30% of cases.

Several radiation catheters, based on the use of radioactive sources such as beta- emitting $^{32}P$, $^{80}Sr/^{90}Y$, $^{188}W/^{188}Re$, beta+ $^{48}V$ or gamma emitting $^{192}Ir$, are at various stages of development and implementation. These radioactive sources, in a variety of configurations, are introduced via special catheters into the blood vessels and the radioactive source is placed at the treatment position for a predetermined period for obtaining the proper irradiation dose. Typical doses required for the treatment are between 10–20 Gy (1,000–2,000 rem). Another method utilizing a radioactive source is the implantation of a radioactive stent based on the above radioactive isotopes.

In these methods there is limited ability to provide selective control of time dosage or radiation intensity. These methods include exposing healthy organs to dangerous radiation during the introduction of the radiation source and require handling radioactive materials which involves hazards to both the individual handling the radioactive materials and to the environment.

X-ray radiation is typically produced by high energy electrons generated and accelerated in a vacuum to impact on a metal target. The efficiency of x-ray generation is dependent on the electron beam current and on the acceleration voltage. An emitted x-ray spectrum is composed in part of discrete energies characteristic of transitions between bound electron energy levels of the target element. The spectrum also includes an x-ray energy continuum, known as bremsstrahlung, which is caused by deceleration of the beam of electrons as they pass near target nuclei.

Another method for the production of x-rays is by direct conversion of light into x-ray radiation. It is known that the interaction of light with a target can produce highly energetic x-rays when the power densities achieved are in the range of $10^{18}$-$10^{17}$ watt/cm$^2$. With the development of femtosecond laser, such power densities are achievable with moderate size lasers (for example see C. Tillman et al, NIMS in Phys.Res. A394 (1997), 387–396 and references therein and U.S. Pat. No. 5,606,588 to Umstadter et al.). For example, a 100 femtosecond pulse of 1 mJ laser pulse focused down to a 3 micron spot, will reach this power density level. Medical applications of this method of x-ray generation are currently in development stage. These methods of x-ray generation have been considered for medical imaging [Herrlin K et al. Radiology (U.S.A.), vol189, no1, pp. 65–8, October 1993]. Another medical application of femtosecond lasers is in improved non-thermal ablation of neural or eye tissue for surgical purposes. [F. H. Loesel et al. Appl.Phys.B 66, 121–128 (1998). The development of compact table top models of femtosecond lasers makes the radiotherapy application of laser generated x-rays an attractive alternative.

U.S. Reissue Pat. No. 34,421 describes a miniature x-ray source for oncological application based on a glass tube incorporating a tungsten anode and a heated thermionic cathode and alternatively a field emission cathode. U.S. Pat. No. 5,737,384 to Fenn describes an apparatus useful for the treatment of tumors in a patient's body by radiotherapy, which utilizes the traditional method of x-ray generation based on acceleration of electrons emitted from a thermionic cathode situated externally to the treated volume. The electrons are accelerated through a thin hollow needle toward the anode placed in the treatment area. U.S. Pat. No. 5,729,583 to Tang et al. relates to a miniature x-ray source for radiotherapy which utilizes several types of field emission, ferroelectric and solid state thermionic cathodes, U.S. Pat. No. 5,428,568 to Oettinger et al. describes an x-ray source with a flexible fiber optical cable, utilizing a light pulse for the generation of an electron pulse from a photocathode located at the end surface of the optical cable. U.S. Pat. No. 5,684,822 describes a miniature x-ray device based on a cold cathode emission electron source.

All above cited patents describe devices for generation of x-rays in energy range from 10 60 keV. While fit for their intended purpose, such devices lack one or more of the following features: the capability of obtaining high fluxes of x-rays, capability to miniaturize devices in size, minimization of the quantity of heat produced during the x-ray generation process and the capability of efficient removal of generated heat.

OBJECTS AND SUMMARY OF THE INVENTION

It is the object of the present invention to provide a miniature x-ray device for brachytherapy with improved performance in the above listed design objectives.

It is another object of the present invention to obtain relatively high fluxes of x-rays.

It is yet another object of the present invention to provide devices miniature in size capable of insertion through the cavities of a living body.

Another object of the present invention is to minimize the quantity of heat produced during the x-ray generation process and the efficient removal of such generated heat.

The present invention provides a radiotherapeutical device useful for brachytherapy, comprising a light source, a wave guide and an x-ray source for the in situ generation of x ray. A very high intensity x-ray pulse is achieved due to the unique geometry in which the electrons are accelerated toward a control elongated anode in the device. Furthermore, the device of the present invention may utilize the method of direct conversion of light into x-ray radiation, providing a radiotherapeutical device with no need for accelerating an electron beam and with no need for electric conductors, thereby greatly simplifying its operation. In accordance with the special geometry of the present device, the x-ray source, and consequently the wave guide comprising said x-ray source's diameter can be made smaller than the devices of the art (<3 mm) to enable introduction into smaller blood vessels or implantation in smaller volumes. In the present invention the use of short light pulses enables, the use of high voltage pulse generators synchronized with the light pulse for short high voltage duration, thus minimizing discharge problems.

The present invention relates to a radiotherapeutical x-ray source comprising a target, such as metallic tungsten, molybdenum, gold, metal alloys or rare gases, in which x-ray radiation is generated by direct conversion of a laser light pulse interacting with the target.

The present invention provides for a radiotherapeutical device comprising a light source, a wave guide and an x-ray source for the in situ generation of x-ray in the device the light source is at a proximal end of the wave guide, preferably located externally to a treated area and the x-ray source is at a distal end of the wave guide, preferably located at a treated area. The x-ray source is preferably located in a capsule, which may be a disposable unit. The wave guide may be a thin needle or a small diameter (<1 mm) flexible guide and capsule diameter may be of diameter of 2 mm and smaller.

According to one preferred embodiment of the device the light source is a pulsed laser and the x-ray source is a target (either in gaseous or solid state) in which x-ray radiation is generated by direct conversion of the laser light pulse interacting with the target. The target is located in a capsule at the distal end of the wave guide and the laser light pulse, traveling through the wave guide to the target, may be a pulse in the range of 100–500 femtosecond, which when focused, produces power densities in the range of $10^{16}$-$10^{17}$ watt/cm$^2$. For example, A 100 femtosecond pulse of 1 mJ laser pulse focused down to a 3 micron spot size, reaches a power density in the range of $10^{16}$-$10^{17}$ watt/cm$^2$.

According to another preferred embodiment the radiotherapeutical device further comprises a power supply or a pulse generator and conductors from the power supply or pulse generator which are connected to the x-ray source; wherein the x-ray source, comprising a photocathode and an anode, is located in a capsule at the distal end of the wave guide. The photocathode and anode of the present device differ from those of the devices in the art in that the photocathode is at the bottom or distal end of the capsule, and the x-ray emitting anode is at the proximal end of the capsule, opposite the cathode. In this embodiment the electron emitting target is not located at the end surface of the optical wave guide, as is the case in the devices in the art. The photocathode is shaped to maximize the area for the photoemission of electrons in the direction of the anode, such as concave shaped, and the anode, which is at the proximal end of the capsule, opposite the cathode, is shaped in an optimal geometry such as a conical needle or hemisphere to produce desired radiation contours for specific types of treatment and radiation. According to this embodiment the light source may also be a high intensity flash lamp and the photocathode may be made of metallic gold, gallium arsenide or any other photoemissive material.

According to another preferred embodiment the electron source is comprised of a miniature photodiode placed at the distal end of the capsule and coated by a thin photoemissive layer. The operation of the laser photodiode will generate a current of electrons which are accelerated to the high voltage anode to produce x-rays.

According to another preferred embodiment the device comprises a plasma discharge electron source placed at the proximal end of the capsule. Electrons produced from this source are accelerated toward the anode placed at the distal end of the capsule.

According to another preferred embodiment the device comprises a laser heating electron source. Electrons are produced by direct heating by a focussed laser pulse and accelerated toward the anode. The heating target comprises a thin metallic coating (2000 Angstroms) on a transparent substrate placed at the proximal end of the capsule. Electrons generated by the laser pulse are accelerated toward the anode to produce x-rays. Typical laser pulses used in this device are 5 ml, 10 nsec Nd-YAG laser pulses at repetition rate of 10 pulses per second (pps). It is contemplated herein to have a range of pulses.

According to another preferred embodiment the laser heating target is placed at the distal end of the capsule and the laser pulse is focussed on the target through a hollow anode. Electrons produced by laser heating are accelerated toward the anode by the high voltage to produce x-rays.

The present invention further relates to a method for the generation of x-rays in situ in the human body, comprising locating the x-ray source of the device, preferably by inserting it into a body cavity, such as a blood vessel, at a treated area, and according to one embodiment activating the light source and, according to another embodiment, concurrently activating the power supply. This method is useful in a wide range of brachytherapy procedures and the x-ray source may be inserted into body cavities via a catheter in combination with medical procedure instrumentality, such as balloons or stents.

BRIEF DESCRIPTION OF THE DRAWINGS

The present invention will be understood and appreciated more fully from the following detailed description taken in conjunction with the appended drawings in which:

FIGS. 4A–4C.

FIGS. 5A–5D.

FIGS. 9A–9C.

FIGS. 10A–10B.

DETAILED DESCRIPTION OF THE PREFERRED EMBODIMENTS

The present invention relates to miniaturized x-ray tubes, that enable radiation treatment by locating the x-ray source within a human body in close vicinity to or inside of the area to be treated with X-rays. Advantageously, the present invention eliminates most of the problems related to the methods based on a radioactive source and offers a method for efficient and controllable radiation treatment. The present invention uses: much lower voltage than known devices, pulsed heat and high flux so as to reduce the heat which is produced and thus shortening treatment time of the subject.

The design of this x-ray source offers a robust solution suitable to size reduction down to diameters of 1 mm. This will allow access to very narrow blood vessels. The design of the electron emitter and high voltage anode allow for very efficient collection of electrons. This compared with conventional devices in which the design of the electric field and the possibility of charge leakage does not insure this kind of efficiency. In the solutions based on field emission electron sources the electron current depends strongly on the applied field and a time variability of the x-ray output is expected. In the present invention, the electron current is field independent and allows the change of the energy of x-rays without influencing the flux.

Figure 1:
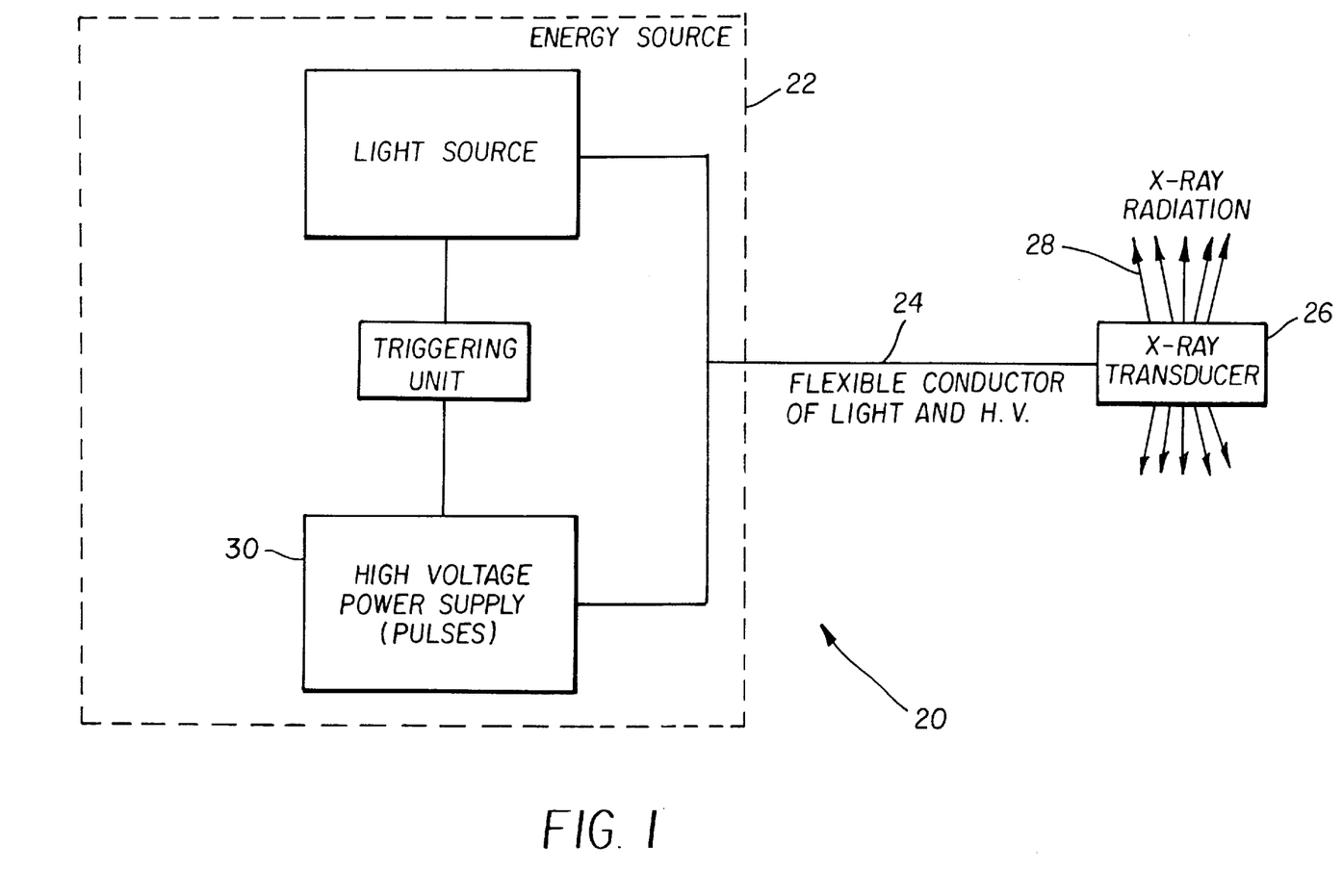
FIG. 1: A functional block diagram of the present invention.

With reference to the drawings for purposes of illustration, the present invention generally relates to a device 20 comprising an energy source 22 coupled to a delivery conduit 24 to deliver energy from the energy source 22 to a miniature energy transducer 26 located at a proximal end of the conduit. The transducer 26, functioning as an X-ray source, converts the energy from its transmitted form into X-ray radiation and distributes the radiation, illustrated by arrows 28, in a predetermined distribution pattern. Advantageously, the present invention has application in a wide range of minimally invasive brachytherapy procedures such as intravascular irradiation treatment for the prevention of restenosis following angioplasty, treatment of organs and implantation in organs, tumor irradiation and other irradiation applications in the human body. Preferably the energy source 22 is located externally to the treated area and the transducer 26 is located generally at the treated area. In general, the energy source 22 may be adapted to provide electrical or optical energy through the conduit 24 that is correspondingly configured to deliver the energy to the transducer 26. Accordingly, the transducer 26 configuration also varies in relation to the characteristics of the energy used. As discussed below, the transducer 26 may be configured to derive power from the energy source 22 or from an independent power supply. For transducers requiring an independent power supply, the device further comprises a power supply 30, such as voltage pulse generator, located externally to the treated area, connected through conductors included in the conduit 24 to the transducer 26. The transducer functions as an X-ray source and the use of the term X-ray source as used throughout this application refers broadly to transducers that convert energy into X-ray radiation.

The X-ray source is preferably surrounded by X-ray transmissive insulation to present direct contact with the human body. Such insulation may be in the form of a capsule located at the proximate end of the conduit. The configuration of the conduit may vary to permit selection the conduit features by the treating physician. Conduit variations can include a rigid or semi-rigid hollow tube, such as a needle for insertion into tumors, or preferably flexible, such a catheter that is capable of following the contours of a blood vessel or any other body cavity. The insulated X-ray source is preferably replaceable and disposable unit for avoiding complex sterilization processes.

Figure 3:
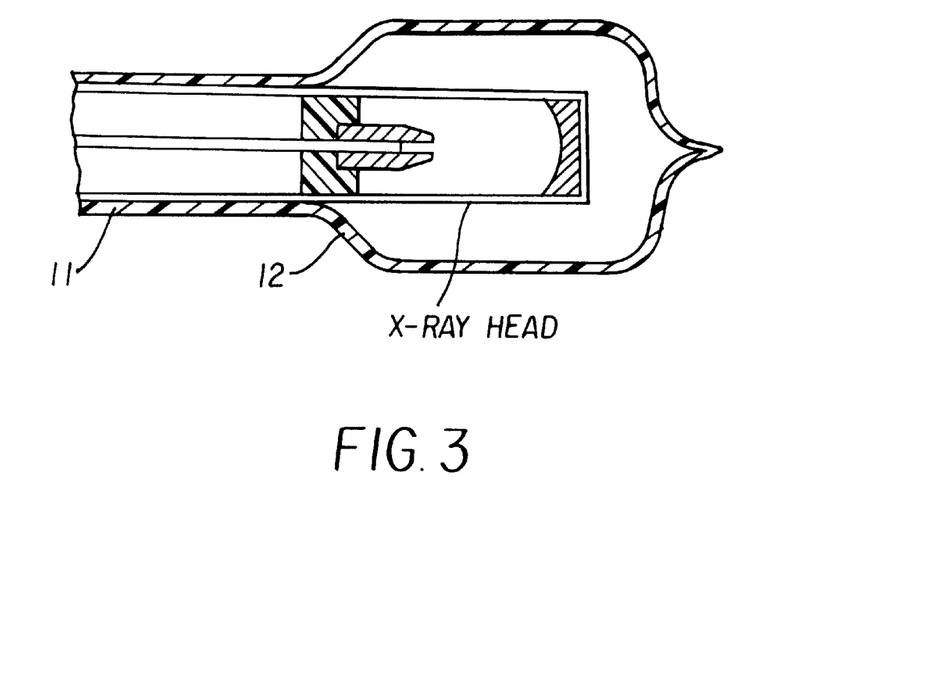
FIG. 3: A diagrammatic view of the x-ray capsule combined with an angioplasty balloon.

FIG. 3 shows the wave guide (11) of the present invention in combination with medical procedure instrumentality, such as a balloon (12) for angioplasty in coronary blood vessels, whereas x-ray can be generated and the patient be irradiated simultaneously with the angioplasty procedure.

Figure 2:
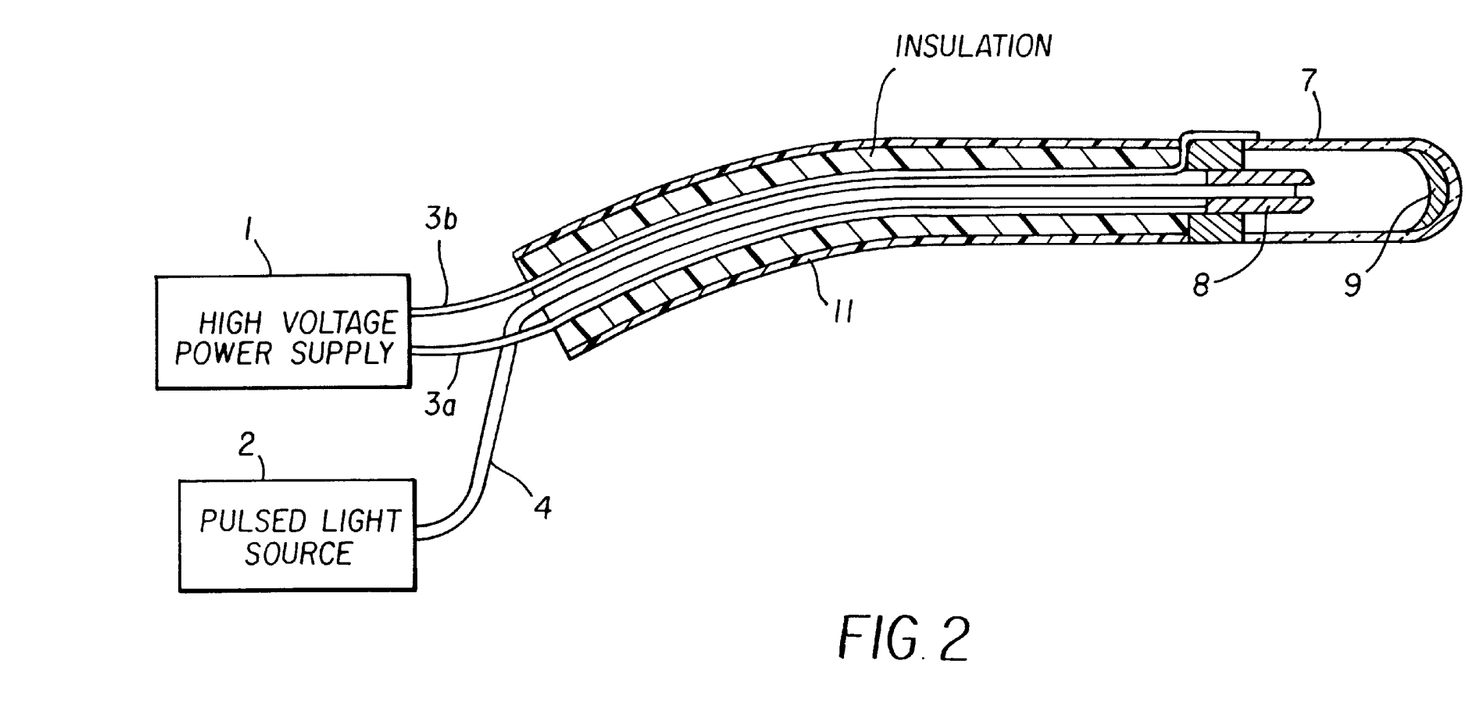
FIG. 2: A diagrammatic view of the device according to a preferred embodiment of the present invention.

With reference to FIG. 2 diagrammatically illustrating a preferred embodiment of the invention, the x-ray source, housed in a capsule 7 having an evacuated chamber, has a photocathode 9 at the bottom or distal end of the capsule 7, opposite an optical element 12 (FIG. 4a) transmitting energy in the form of light emitted from a light source 2 through the conduit in the form of a wave guide 11.T As defined herein the "optical element" is a beam shaping system connected to a converting element which emits electrons. The electrons may be generated by photoemission, plasma, laser heated or direct conversion. The waveguide terminates in one embodiment by an optical element 13 (FIG. 5a) to focuss the light beam. The light, transmitted as a pulse, may be obtained from a pulse laser or from a high intensity flash lamp. The photocathode 9 is made of highly efficient photo emissive material, with an optimal wave length efficiency response, conventional materials of the type suitable for this purpose include, but are not limited to, metals, such as Au, Mg, Cu, semiconductors, like gallium arsenic, and compounds, such as Cs3 Sb, Cs2 Te, and AgOCs. It will be appreciated by those skilled in the art that such photoemissive materials vary in efficiency and in operating conditions, such as vacuum requirements and the light wave length of the light source. However, such parameters are known to those skilled in the art. The photocathode 9 is concave shaped for optimal emission of electrons in the direction of the anode 8 which is at the proximal end of the capsule 7, opposite the cathode 9, so that it receives the electrons emitted from the cathode 9. The anode 8 is charged to a high voltage (10–50 kV) by means of one of the conductors 3a, 3b from the voltage power supply 1 or voltage pulse generator, and the photocathode 9 is kept, together with the capsule 7, at ground potential. With reference to FIG. 5A, the optical fiber (4) runs through the elongated anode (8) and is terminated in an optical element (13) which directs the light rays (18), traveling through the optical fiber, to the photocathode (9). The photocathode emits electrons (14) which are accelerated in the direction of the anode due to the acceleration potential applied by the high voltage conductor (3a) connected to the anode. The anode 8 is shaped in an optimal geometry to produce desired radiation contours for specific types of treatment and radiation delivery. Examples of such anode shapes can be for instance conical shape for cylindrical pattern of radiation, hemispherical for radial shape and flat surface for directing toward a particular orientation. Other assymetrical radiation patterns are possible as well. These kinds of geometries were described in U.S. Pat. No. 5,729,583 to Tang et al. (incorporated hereinafter by reference).

According to this embodiment, voltage is applied by the external power supply 1 and the emitted electrons are accelerated by the applied voltage toward the positively charged anode 8 and produce an x-ray pulse. The anode is located distal to the wave guide or capsule's end surface. The achieved x-ray spectrum consists of bremstrahlung and characteristic x-rays of the anode material (K$\alpha$). The Intensities and conversion efficiencies of the emitted radiation are suitable for the envisioned applications of this invention. The power supply has electrical conductors (3a and 3b) exiting from it connected to or running along the wave guide (11) through insulation (10) which comprises the inner surface area of the wave guide (11). One of the electrical conductors is a high voltage lead (3a) and the other (3b) is for keeping the photocathode (9) and the capsule (7), at ground potential. The pulsed light source (2) has an optical fiber (4) made up of a core and cladding exiting from it and running through or in between the wave guide insulated walls (10).

Figure 4A:
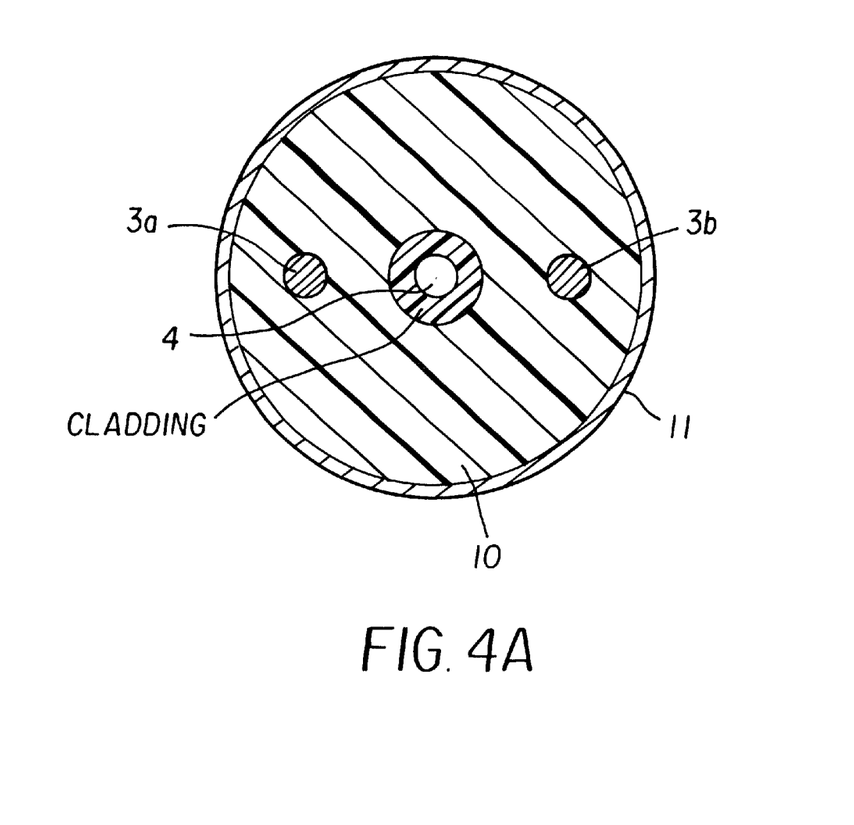
FIG. 4A is a cross section of the wave guide substantially along line 1—1 of FIG. 2 in which a single optical fiber is used.
Figure 4B:
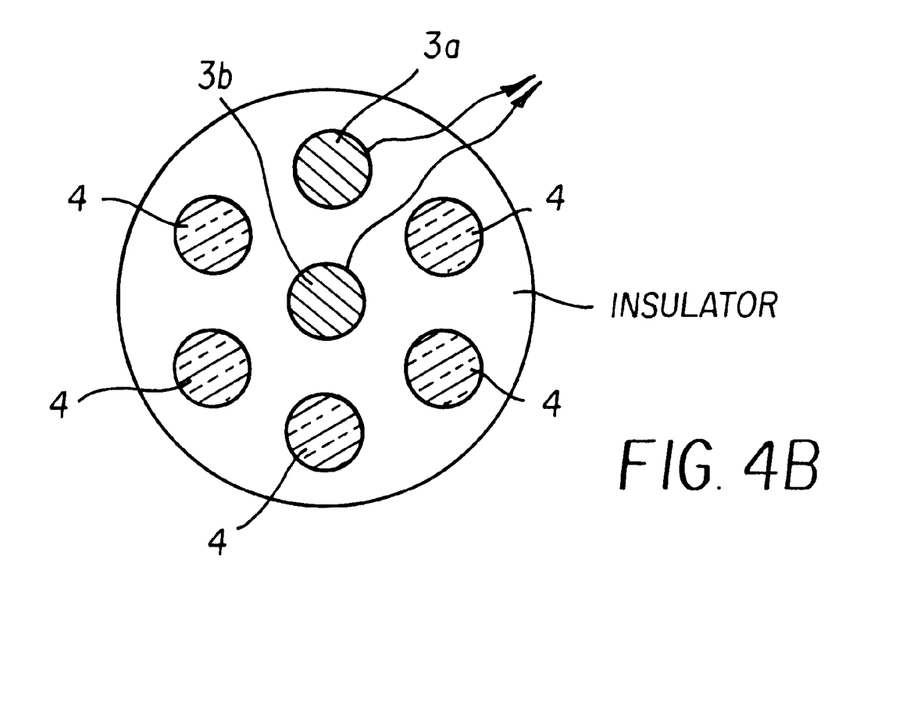
FIG. 4B is a cross section in which several optical fibers (bundle) comprise the flexible guide.
Figure 4C:
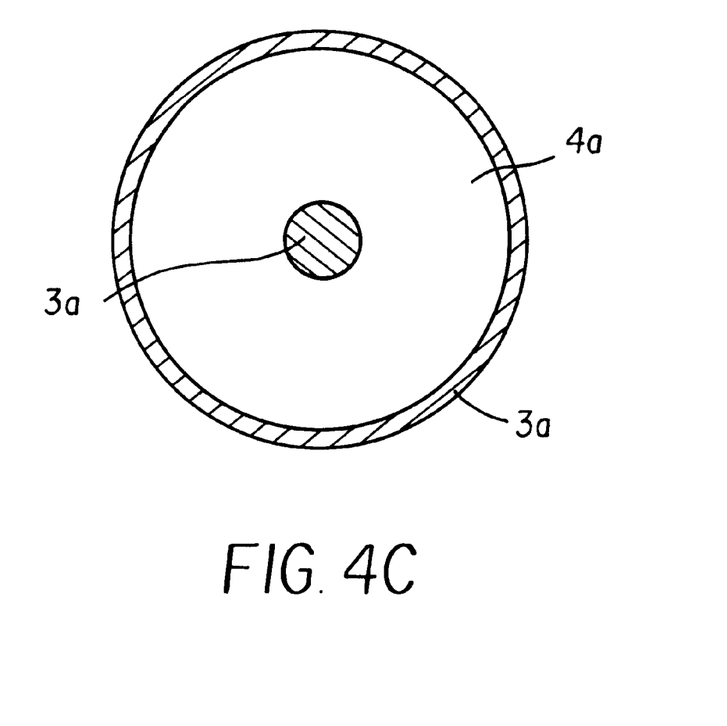
FIG. 4C is a cross section of the flexible guide in which a hollow optical guide is employed.
Figure 5A:
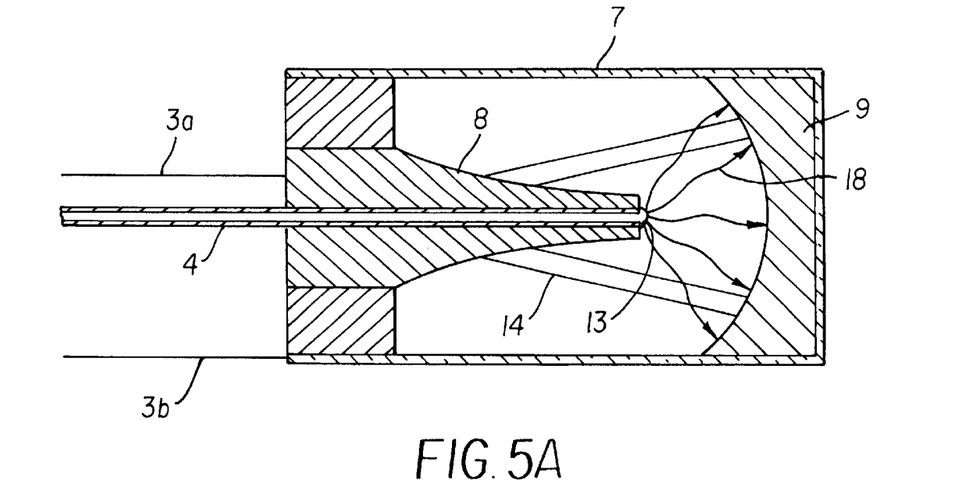
FIG. 5A shows an enlargement of the capsule containing the x-ray head according to three embodiments of the present invention as shown in FIGS. 4A–4C.
Figure 5B:
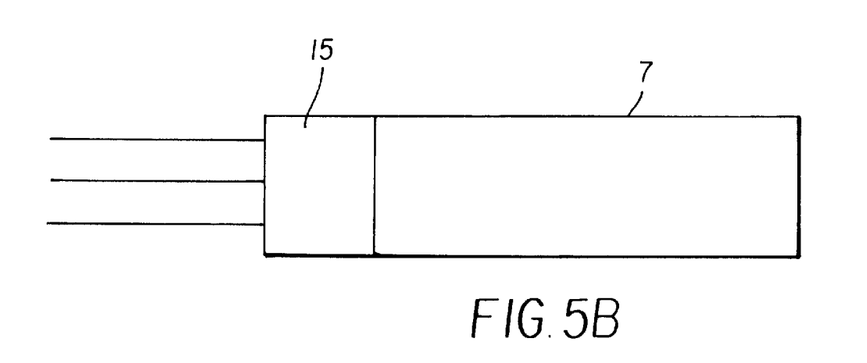
FIG. 5B shows a preferred embodiment of the present invention in which the x-ray capsule terminates with a special coupler.
Figure 5C:
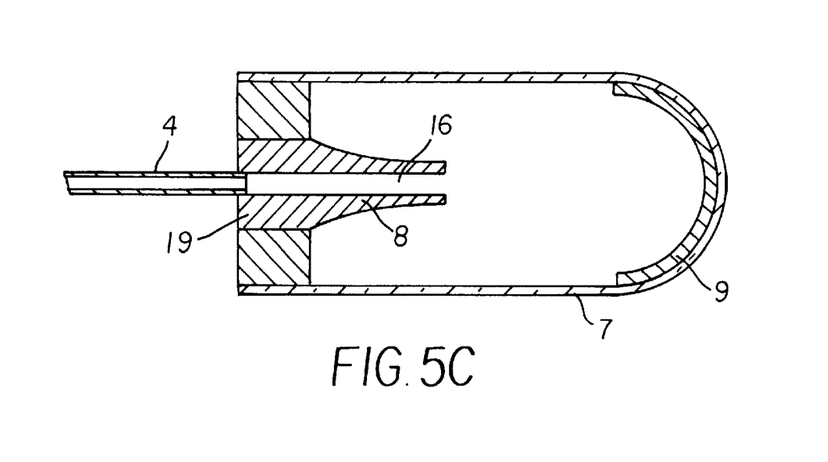
FIG. 5C shows another embodiment in which the optical guide (fiber) terminates at the entrance to the hollow anode.
Figure 5D:
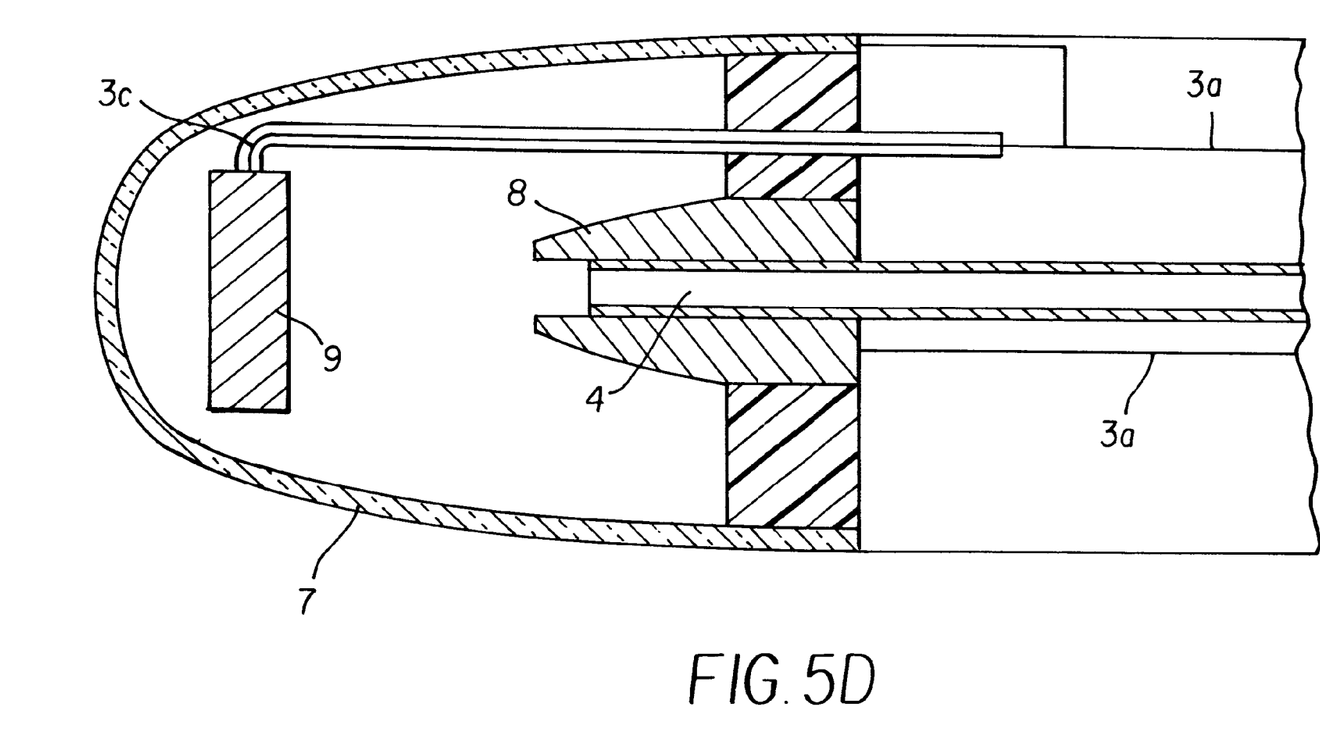
FIG. 5D shows another embodiment in which the photoemissive target is suspended inside the ampoule.

With reference to FIG. 4 (4A–4C), the wave guide of the present invention includes the insulation (10) which surrounds the metal leads and incorporates the optical wave guide. The electrical conductors (3a and 3b) run through the insulation and are maintained in a spaced apart relation. Several solutions exist to insure the proper high voltage insulation together with the optical fiber. Fiber of diameter of 100 microns are capable of supplying the required optical energy. High voltage coaxial cable with diameters down to 1 mm can withstand the high voltage pulses of this device. Such cables are commercially available for example from New England Electric Wire Corporation, Lisborn, N.H. as cited by V. I. Chornenko in U.S. Pat. No. 5,854,822 which is incorporated by reference. By combining the coaxial cable and the optical fiber in one shroud a flexible guide is produced. Another possibility is to produce a custom made flexible guide which incorporates the fiber optic and conductors in one insulated cable with diameter of approximately one millimeter.

FIG. 5 illustrates the special geometry of the anode of the x-ray source of the device of the present invention. In FIG. 5A the optical fiber (4) runs through the elongated anode (8) and is terminated in an optical element (13) which directs the light rays (18) traveling through the optical fiber, to the photocathode (9). The photocathode emits electrons (14) which are accelerated in the direction of the anode due to the acceleration potential applied by the high voltage conductor (3a) connected to the anode. In FIG. 5B the optical fiber (4) is terminated at the entry (19) to the capsule (7) and does not run through the elongated anode (8), rather the light rays traveling through the optical fiber are transmitted through a hollow tube (16) running through the elongated anode (8). In another embodiment, the wave guide 11 of FIGS. 2 and 3 includes a single 100 micron diameter fiber or a multiplicity of fibers arranged randomly or ordered in a bundle with metal conductor wires being a part of the bundle as in FIG. 4B. Alternatively being comprised of a hollow glass or silica fiber with the high voltage metal conductor at the center and the grounded conductor on the periphery as in FIG. 4C.

According to another preferred embodiment (FIG. 6), the transducer includes a target material 17 that may be located at the end surface of the wave guide 11 or on the capsule 7 which comprises the wave guide's end and the light traveling through the wave guide interacts directly with the target, generating x-rays by direct emission of x-rays from the hot plasma produced by the light pulse interaction with the target material 17. The target material may be in solid or gaseous form, of any material suitable for emitting x-rays upon direct interaction with a pulse of light, such as metal alloys, metallic tungsten, molybdenum, gold or any of the rare gases. In this process very high efficiency of energy conversion can be obtained. Pulses in the range of 100–500 femtosecond, when focused, produce power densities in the range of $10^{16}$-$10^{17}$ watt/cm$^2$. For example, a 100 femtosecond pulse of 1 mJ laser pulse focused down to a 3 micron spot size, reaches a power density in the range of $10^{16}$-$10^{17}$ watt/cm$^2$. Since the conversion efficiency of laser energy to x-rays under these conditions is very high (0.5% for energies above 10 keV), very high x-ray doses (10–20 Gy) are achievable in short exposure times (tens of seconds).

Figure 6:
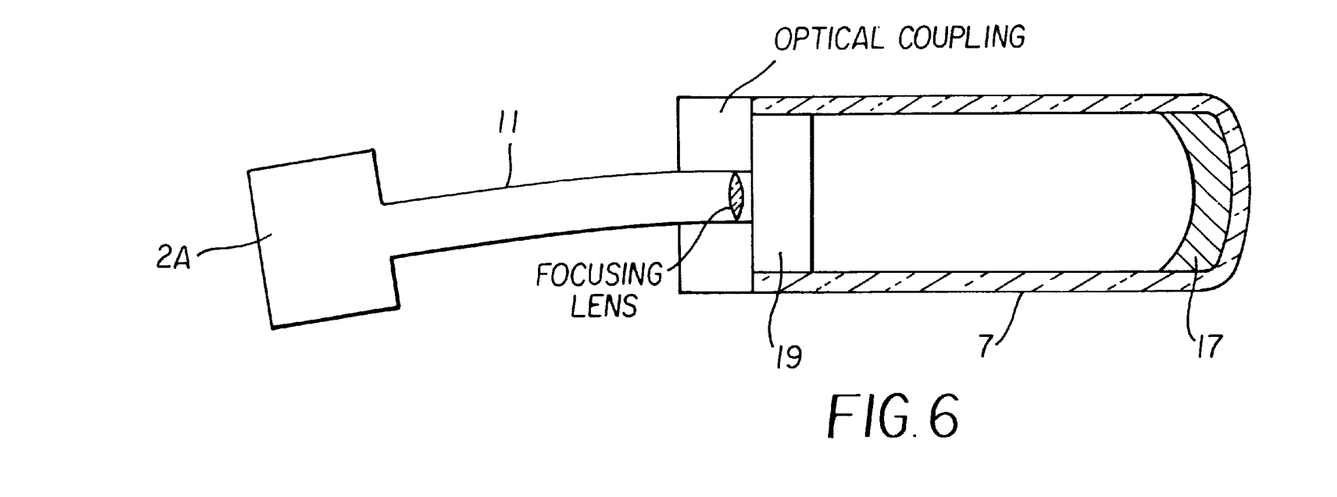
FIG. 6: Shows a diagrammatic overview of a preferred embodiment in which direct conversion of light into x-rays occurs.

The light pulse is generated by a light source in wave lengths which are optimized to the target material, and is fed into the light guide through an optical focussing system. The light pulse exits the light guide at the distal end and enters the capsule through another focusing system which focuses the light pulse on the target.

Figure 7:
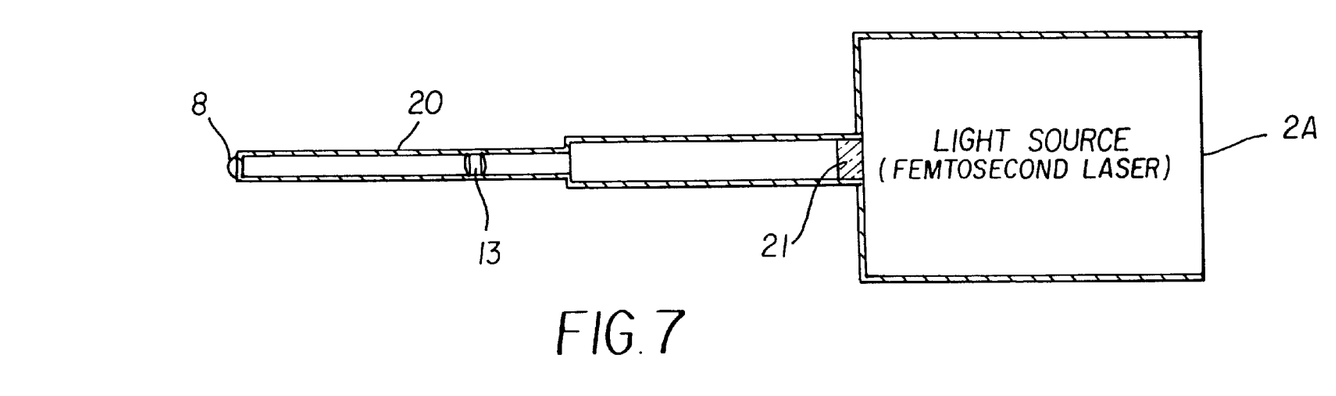
FIG. 7: shows another embodiment of FIG. 6 in which the optical guide is a needle.

FIG. 7 illustrates yet another embodiment of the present invention. In this embodiment the wave guide 11 is in the form of a needle, especially useful for the treatment of tumors. The pulsed light source (2) is a femtosecond laser, the wave guide (11) is a hollow tube terminating with a hollow needle (20) which has a target (8) at its end. The optical element (13) is a focusing element, such as a lens.

The special design of the device of the present invention which enables a relatively large area of photo emissive material to be illuminated and in which a very high intensity x-ray pulse may be produced, substantially shortens the treatment time. The geometry in which the electrons are accelerated toward a central elongated anode, makes high voltage isolation problems easier. In accordance with the special geometry of the target configuration, the capsule, and consequently the wave guide comprising said capsule, diameter can be made smaller than the devices of the art (<3 mm) to enable introduction into smaller blood vessels or implantation in smaller volumes.

In the present invention, the high current pulse generated by the electron photoemission enable the use of high voltage pulse generators as the high voltage source, thus minimizing discharge problems. The device may comprise a disposable x-ray generating capsule thus avoiding complex sterilization processes. The device enables the rationing of radiation dose delivery in situ and may be implanted for multiple irradiation treatment and follow up of the treatment progress.

The present invention further relates to a method for the generation of x-rays in situ in the human body, preferably for application in a wide range of brachytherapy procedures, for minimally invasive radiation treatment of tumors and intravascular x-ray irradiation treatment for the prevention of restenosis in the human body. The method comprises locating the x-ray source of the device of the invention, preferably by inserting the x-ray device of the invention to a human body cavity, such as blood vessel, and activating a light source, and optionally activating a power supply, according to the embodiments of the invention. The device may be inserted in to a body cavity or to any location in the body during any medical procedure, such as angioplasty in coronary blood vessels, in combination with medical procedure instrumentality, such as balloons and stents. The method of the present invention is useful in a wide range of brachytherapy procedures. By way of example, FIG. 2 shows the wave guide (11) of the present invention in combination with medical procedure instrumentality, such as a balloon (12) for angioplasty in coronary blood vessels, whereas x-ray can be generated and the patient by irradiated simultaneously with the angioplasty procedure.

Figure 8:
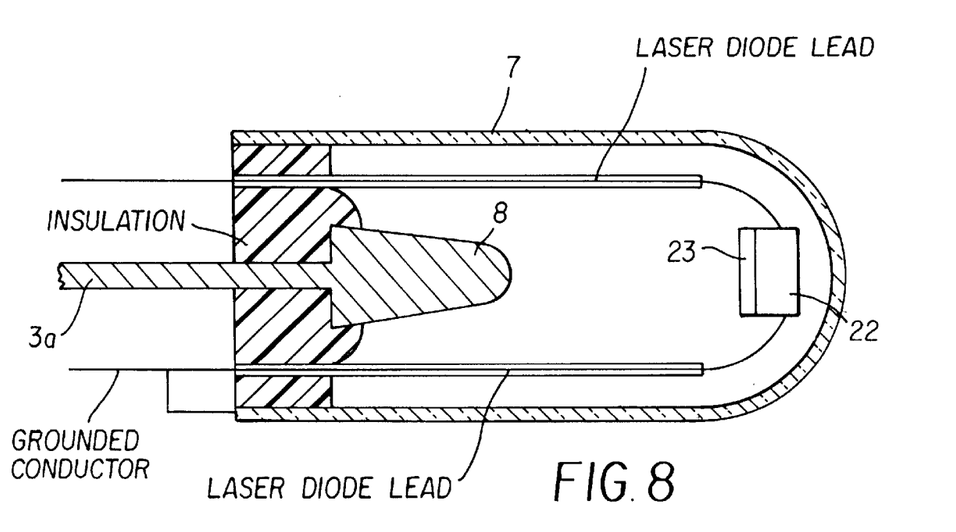
FIG. 8: shows an embodiment of the invention based on a laser diode electron source.
Figure 8A:
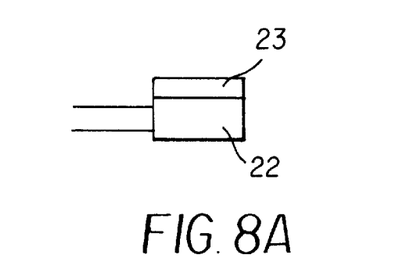

In another embodiment, the photoemitter as shown in FIG. 8 consists of a GaAs laser diode coupled to a GaAs photoemissive layer. The leads which supply the necessary voltage to operate the diode are conducted along the walls of the capsule by insulated wires. By operating the laser diode the laser light will generate a current of electrons from the photoemissive coating. The electrons will be accelerated to the anode by the high voltage. In this case the ampoule can be made either of metal or of insulating material like ceramics or glass. In another embodiment the photoemissive cathode is suspended in the capsule from a grounded conductor insulated in a thin tube. In this case the ampoule can be made either of metal or of insulating material like ceramics or glass. The wave guides used in all embodiments may be chosen to conduct light in the range from near Infra Red to Ultraviolet or be selected for the specific wave length interval as required by the properties of the photoemissive material.

Figure 9A:
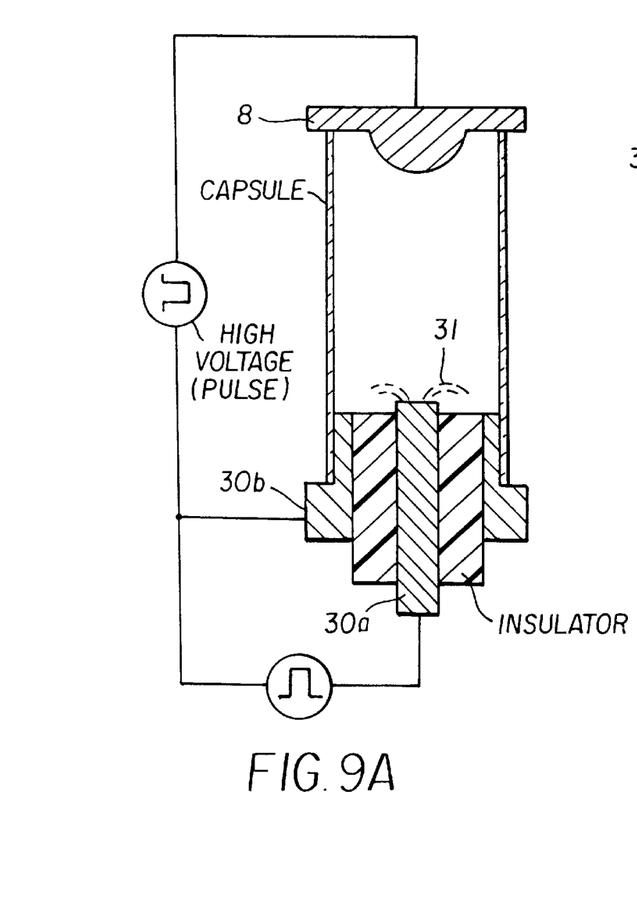
FIG. 9A shows an embodiment of the invention based on a plasma discharge based electron source.
Figure 9B:
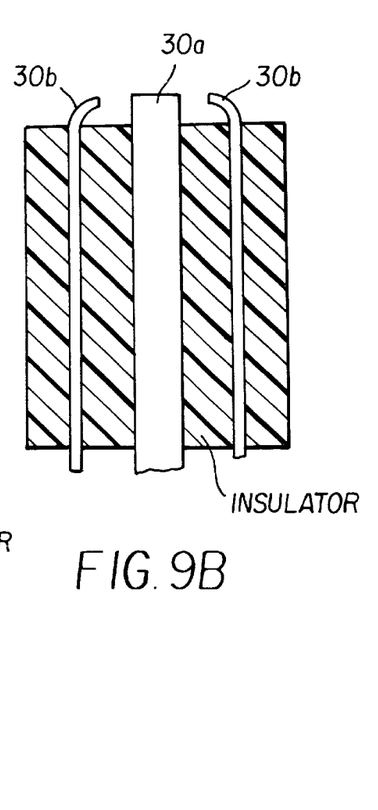
FIG. 9B shows the electron source in detail.

Another embodiment of a miniature x-ray source as shown in FIG. 9 is based on the application of a plasma cathode electron source. Such methods of emission of electrons have been studied by Y. Ehrich et al. [Phys.Rev.Lett. 77,4186 (1996) and references therein]. The electron source consists of several concentric capillaries as shown in detail in FIG. 9b: a metal capillary about 200 micron diameter (electrode 30a) inserted in a 100 micron thick insulating capillary and surrounded by a concentric metal capillary (electrode 30b). By applying a high voltage between the metallic electrodes a plasma discharge is produced on the surface of the insulating capillary 30C and electron emission occurs. This method produces high intensity electron pulses and can be operated for many cycles. Such produced electrons are accelerated toward the anode to generate x-rays. This x-ray emitter has shown very high efficiency. For example a 10 nsec voltage discharge of 20 kV and an accelerating voltage of 20 kV resulted in the emission of 5E9 x-ray photons from an anode made of CuZn (brass) aloy. The energy generated in the plasma discharge was 4 mjoule per pulse.

Figure 9C:
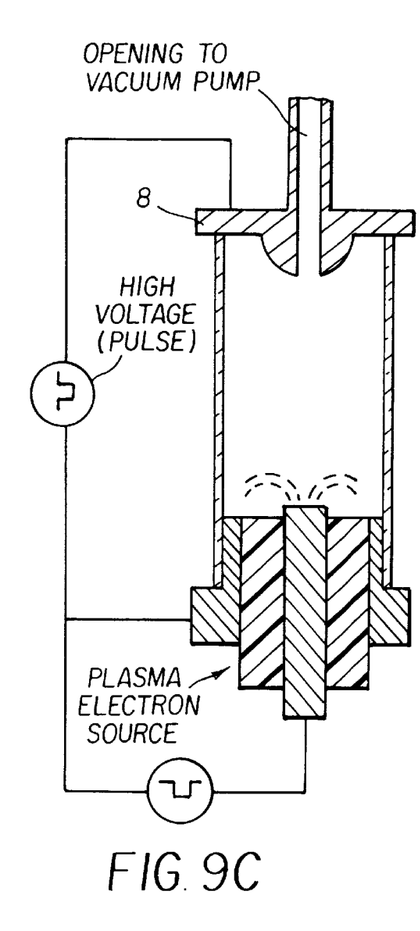
FIG. 9C shows the x-ray source with the possibility of dynamic pumping.

FIG. 9C presents a particular embodiment of this type on an x-ray source in which the anode is hollow enabling connection to a vacuum pump for dynamic pumping during the operation of the x-ray source.

Figure 10A:
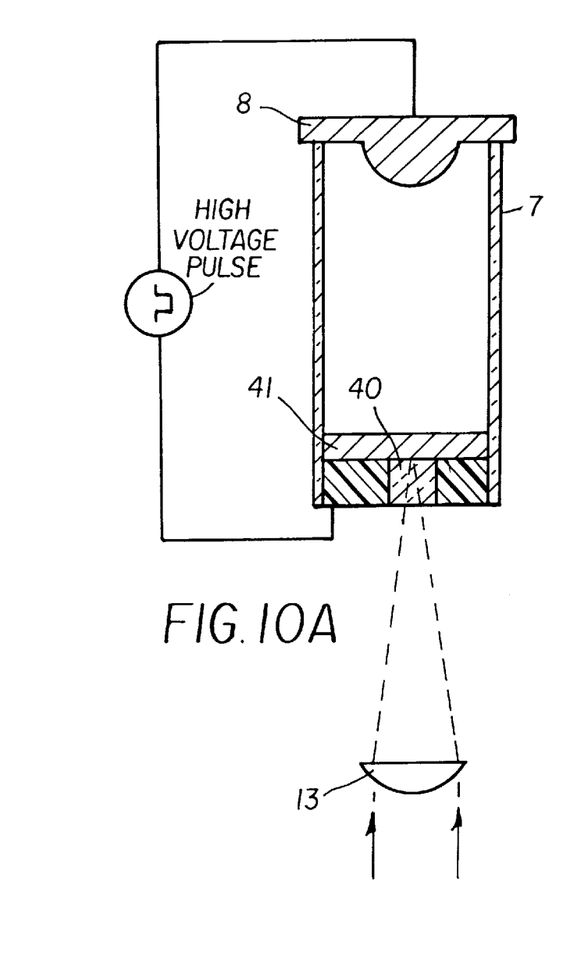
FIGS. 10A and 10B show two embodiments of the invention based on a laser heating electron source.
Figure 10B:
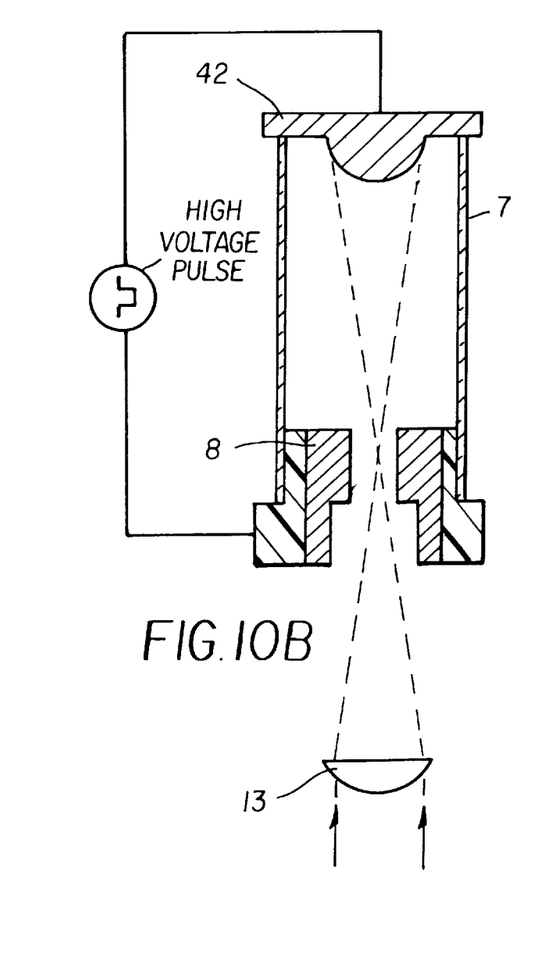

Another embodiment of this invention is presented in FIG. 10A. In this embodiment the electron source is comprised of a thin metallic layer 41 coated on a transparent optical window 40. A laser pulse focussed by an optical element (lens) 13 heats the metal target and causes the target to emit electrons. These electrons are accelerated by a High Voltage pulse (20–50 kV) toward the anode 8 and generate x-rays. The thickness of the metal layer 41 is approximately 2000 Angstroms and the laser energy is 5 mj per pulse. The pulse rates required to obtain the x-ray flux is of the order of 10 pulses per second. FIG. 10B shows another embodiment of the invention in which the heated target 42 is placed at the distal end of the capsule and the laser pulse is guided through a hollow anode 8 located at the proximal end of the capsule. The opening of the hollow anode can be used for dynamic pumping.

As previously stated this invention is directed toward application in brachytherapy, the main applications beeing radiosurgury in oncology and endovascular brachytherapy for the treatment of restenosis. Other applications, which have been considered are applications in which a very specific area and depth of penetration are needed. Examples of such treatment are the treatment of GERD (Gastroesophageal Reflux Disease) and Menorrhagia.

It is desirable in the field of brachytherapy treatment to control the radiation dose estimate. By incorporating into the guiding catheter additional conducting leads it is possible to monitor in real time the radiation dose delivered A sensor suitable for this application is for example a RADFET manufactured by ESA-ESRIN real time integrating dosimeter, which can be mounted together with the radiation capsule. Another possibility is to incorporate a miniature MOSFET detector (produced for example by Thomsom and Hielson, Ottawa, Canada) or a Scanditronix p-type semiconductor detector (produced by Scanditronix, Uppsala, Sweden.

In operation, the present invention provides a miniture radiation source within the range of 1 to 3 mm capable of traversing through the arterial framework within a living body to position the radiation source at a location suitable for emitting a localized dose of radiation upon target tissue within the living body. When positioned with the living body, the capabilities of the X-ray source may be considered as follows 1. Example of calculation of x-ray generating conditions:
   X-ray dose required for typical treatment of restenosis— 15 Gray
   Time of treatment 300 seconds.
   Dose translated to energy deposited in tissue for a typical case=10 mjoule
   Dose rate=30 microjoule/sec=30 microwatt
   Corresponding X-ray photon rate=2.3 E10 photons/sec in the range between Y-1 1 keV X-ray yield in range of 9-1 keV=1.1E12 photons/mA of 20 kV electron current.
   The current required to produce the needed rate=20 microampere=1.3E14 electrons/sec.
   For photoemission efficiency of 0.1% 3E12 electrons are produced per 1 milijoule of light which translates to 40 1 milijoule pulses per second needed.
   One can use less energetic light pulses at higher repetition rate as for example 400 0.1 milijoule pulses/sec or 4000 10 microjoule pulse/sec.

It will be appreciated by persons skilled in the art that the present invention is not limited by what has been particularly shown and described herein above. Rather the scope of the invention is defined by the claims which follow.

What is claimed is:

1. The radiotherapeutical x-ray device for the treatment of a living body having a localized treatment area comprising:
   an X-ray transducer for the generation of X-ray radiation converted from energy supplied in a predetermined form to said X-ray transducer;
   an energy source that generates said energy; and
   a conduit that supplies said energy to said X-ray transducer from said energy source;

wherein said X-ray transducer includes an element that causes the release of X-rays upon receipt of said energy;

wherein said energy is in the form of light and wherein said element comprises an electron omitting target material positioned to receive said light;

wherein said electron emitting target material comprises a photocathode that is located opposite an anode, and an electrical potential is formed between said photocathode and said anode; and wherein said light is transmitted in a generally linear direction through said conduit and said anode and wherein said anode and photocathode are aligned to direct x-rays circumferentially and perpendicular to the linear direction of the light.

2. A radiotherapeutical device comprising an energy source and conductors from the energy source which are connected to an x-ray source, wherein the x-ray source comprises a photocathode and an anode; wherein the photocathode is at the bottom or distal end of a capsule, and is shaped to emit electrons in the direction of the anode; and wherein the anode is at the proximal end of the capsule, opposite the cathode.

3. A radiotherapeutical device according to claim 2 wherein the photocathode is concave shaped.

4. A radiotherapeutical device according to claim 2 wherein the light source further is a high intensity flash lamp.

5. A radiotherapeutical device according to claim 2 wherein the anode is shaped in an optimal geometry to produce desired radiation contours for specific types of treatment and radiation.

* * * * *